United States Patent
Adams et al.

(10) Patent No.: US 10,272,215 B2
(45) Date of Patent: Apr. 30, 2019

(54) INHALATION TRAINING DEVICE AND SYSTEM FOR PRACTICING OF AN INHALATION PROCESS OF A PATIENT

(71) Applicant: Boehringer Ingleheim International GmbH, Ingelheim am Rhein (DE)

(72) Inventors: Patricia Adams, Ingelheim am Rhein (DE); Marion Frank, Ingelheim am Rhein (DE); Herbert Wachtel, Ingelheim am Rhein (DE)

(73) Assignee: BOEHRINGER INGELHEIM INTERNATIONAL GMBH, Ingelheim am Rhein (DE)

( * ) Notice: Subject to any disclaimer, the term of this patent is extended or adjusted under 35 U.S.C. 154(b) by 213 days.

(21) Appl. No.: 14/676,941

(22) Filed: Apr. 2, 2015

(65) Prior Publication Data

US 2015/0283337 A1 Oct. 8, 2015

(30) Foreign Application Priority Data

Apr. 7, 2014 (EP) .................................... 14001266

(51) Int. Cl.
*A61B 5/087* (2006.01)
*A61M 11/00* (2006.01)
(Continued)

(52) U.S. Cl.
CPC ......... *A61M 15/0021* (2014.02); *A61B 5/087* (2013.01); *A61M 11/007* (2014.02);
(Continued)

(58) Field of Classification Search
CPC ...................................................... G09B 23/28
See application file for complete search history.

(56) References Cited

U.S. PATENT DOCUMENTS

| 5,333,106 A * | 7/1994 | Lanpher ................... G09B 5/02 |
| | | 128/200.12 |
| 5,363,842 A | 11/1994 | Mishelevich et al. |
| | (Continued) | |

FOREIGN PATENT DOCUMENTS

| DE | 202008010475 U1 | 2/2009 |
| EP | 0667168 A1 | 8/1995 |
| JP | 2008532587 A | 8/2008 |

OTHER PUBLICATIONS

MMAudio, "Frequently Asked Questions (FAQ)", http://www.microphonemadness.com/faq.html, undated.

*Primary Examiner* — Eddy Saint-Vil
*Assistant Examiner* — William D Ermlick
(74) *Attorney, Agent, or Firm* — David S. Safran; Roberts Mlotkowski Safran Cole & Calderon, P.C.

(57) ABSTRACT

An inhalation training device and inhalation training system for practicing of an inhalation process of a patient. The inhalation training device has a that is housing attachable to and detachable from a mouthpiece of an inhaler designed to provide a drug to the patient and a microphone adapted to measure the airflow occurring in the mouthpiece of the inhaler during an inhalation process of the patient. The inhalation training system includes the inhalation training device, an inhaler and an electronic device configured for evaluation of a signal received from the inhalation training device and for visual and/or audio feedback to the patient.

8 Claims, 5 Drawing Sheets

(51) Int. Cl.
*A61M 15/00* (2006.01)
*A63B 23/18* (2006.01)
*A63B 21/008* (2006.01)
*A63B 24/00* (2006.01)
*A63B 71/06* (2006.01)

(52) U.S. Cl.
CPC ........ *A61M 15/00* (2013.01); *A61M 15/0068* (2014.02); *A63B 21/0084* (2013.01); *A63B 21/0088* (2013.01); *A63B 23/18* (2013.01); *A61B 2505/09* (2013.01); *A61B 2562/0204* (2013.01); *A61M 2205/02* (2013.01); *A61M 2205/056* (2013.01); *A61M 2205/27* (2013.01); *A61M 2205/276* (2013.01); *A61M 2205/3375* (2013.01); *A61M 2205/3546* (2013.01); *A61M 2205/3561* (2013.01); *A61M 2205/3584* (2013.01); *A61M 2205/3592* (2013.01); *A61M 2205/502* (2013.01); *A61M 2205/52* (2013.01); *A61M 2205/581* (2013.01); *A61M 2205/583* (2013.01); *A61M 2230/40* (2013.01); *A63B 2024/0065* (2013.01); *A63B 2024/0096* (2013.01); *A63B 2071/0625* (2013.01); *A63B 2220/54* (2013.01); *A63B 2225/50* (2013.01)

(56) References Cited

U.S. PATENT DOCUMENTS

| | | | | |
|---|---|---|---|---|
| 5,758,638 | A * | 6/1998 | Kreamer | A61M 15/009 128/200.14 |
| 5,809,997 | A * | 9/1998 | Wolf | A61M 15/009 128/200.23 |
| 5,833,088 | A | 11/1998 | Kladders et al. | |
| 5,839,429 | A | 11/1998 | Marnfeldt et al. | |
| 6,116,233 | A | 9/2000 | Denyer et al. | |
| 6,148,815 | A | 11/2000 | Wolf | |
| 6,358,058 | B1 * | 3/2002 | Strupat | A61B 5/0876 434/262 |
| 6,358,258 | B1 | 3/2002 | Arcia et al. | |
| 6,597,793 | B1 | 7/2003 | Darbut et al. | |
| 6,745,761 | B2 | 6/2004 | Christrup et al. | |
| 6,752,145 | B1 * | 6/2004 | Bonney | A61M 15/009 128/200.23 |
| 6,772,755 | B2 * | 8/2004 | Pera | A61M 15/0028 128/203.12 |
| 7,850,619 | B2 | 12/2010 | Gavish et al. | |
| 8,485,982 | B2 | 7/2013 | Gavish et al. | |
| 8,650,840 | B2 | 2/2014 | Holakovsky et al. | |
| 8,679,061 | B2 | 3/2014 | Julian et al. | |
| 2002/0090601 | A1 | 7/2002 | Strupat et al. | |
| 2003/0041859 | A1 | 3/2003 | Abrams | |
| 2004/0025877 | A1 * | 2/2004 | Crowder | A61M 15/0045 128/203.15 |
| 2004/0094146 | A1 * | 5/2004 | Schiewe | A61M 15/0028 128/200.11 |
| 2004/0187869 | A1 * | 9/2004 | Bjorndal | A61B 5/087 128/203.15 |
| 2005/0247305 | A1 * | 11/2005 | Zierenberg | A61M 15/0065 128/200.14 |
| 2008/0214903 | A1 | 9/2008 | Orbach | |
| 2008/0314380 | A1 * | 12/2008 | Watchtel | A61M 15/009 128/200.23 |
| 2008/0319333 | A1 | 12/2008 | Gavish et al. | |
| 2009/0063773 | A1 | 3/2009 | Rajwar et al. | |
| 2009/0118631 | A1 | 5/2009 | Gavish et al. | |
| 2009/0128330 | A1 * | 5/2009 | Monroe | A61B 50/30 340/568.1 |
| 2009/0245554 | A1 * | 10/2009 | Parker | H04R 25/606 381/326 |
| 2009/0270752 | A1 * | 10/2009 | Coifman | A61B 5/087 600/538 |
| 2009/0308387 | A1 | 12/2009 | Andersen et al. | |
| 2009/0314292 | A1 * | 12/2009 | Overfield | A61B 5/087 128/203.15 |
| 2010/0132699 | A1 | 6/2010 | Burolla et al. | |
| 2010/0160894 | A1 | 6/2010 | Julian et al. | |
| 2010/0192948 | A1 | 8/2010 | Sutherland et al. | |
| 2011/0114089 | A1 * | 5/2011 | Andersen | A61M 15/0091 128/200.23 |
| 2011/0226236 | A1 | 9/2011 | Buchberger | |
| 2011/0226242 | A1 * | 9/2011 | Von Hollen | A61M 15/009 128/203.12 |
| 2012/0107783 | A1 | 5/2012 | Julian et al. | |
| 2012/0116241 | A1 * | 5/2012 | Shieh | A61B 5/082 600/532 |
| 2012/0216805 | A1 * | 8/2012 | Brunnberg | A61M 11/06 128/203.12 |
| 2012/0247235 | A1 | 10/2012 | Adamo et al. | |
| 2013/0008436 | A1 * | 1/2013 | Von Hollen | A61M 15/0086 128/200.14 |
| 2013/0072755 | A1 * | 3/2013 | Papania | A61M 11/005 600/109 |
| 2013/0151162 | A1 * | 6/2013 | Harris | A61M 15/00 702/19 |
| 2013/0206136 | A1 * | 8/2013 | Herrmann | A61M 15/0065 128/200.21 |
| 2013/0289431 | A1 | 10/2013 | Gavish et al. | |
| 2014/0000603 | A1 * | 1/2014 | Hosemann | A61M 15/0028 128/203.21 |
| 2014/0106324 | A1 | 4/2014 | Adams et al. | |
| 2014/0123974 | A1 * | 5/2014 | Edwards | A61M 5/2033 128/200.14 |
| 2014/0204513 | A1 | 7/2014 | Del Padre et al. | |
| 2014/0243749 | A1 | 8/2014 | Edwards et al. | |
| 2015/0037772 | A1 | 2/2015 | Julian et al. | |
| 2015/0122249 | A1 * | 5/2015 | Bowman | A61M 15/009 128/200.23 |
| 2016/0022929 | A1 * | 1/2016 | Cheng | A61M 11/005 128/200.16 |
| 2016/0129182 | A1 * | 5/2016 | Schuster | G06F 19/00 702/56 |
| 2016/0166766 | A1 * | 6/2016 | Schuster | G06F 19/3468 702/54 |
| 2016/0228657 | A1 * | 8/2016 | Sutherland | A61M 15/009 |
| 2016/0363582 | A1 * | 12/2016 | Blackley | G01N 33/497 |
| 2017/0100550 | A1 * | 4/2017 | Van De Laar | A61M 15/0021 |
| 2017/0119982 | A1 * | 5/2017 | Jones | A61M 15/0043 |

* cited by examiner

INHALATION TRAINING DEVICE AND SYSTEM FOR PRACTICING OF AN INHALATION PROCESS OF A PATIENT

BACKGROUND OF THE INVENTION

Field of the Invention

This invention relates to an inhalation training device for practicing of an inhalation process of a patient, and to an inhalation training system for practicing of an inhalation process of a patient.

Description of Related Art

Drugs which are to be inhaled constitute a preferred therapy for patients with asthma, a chronically obstructive pulmonary disease or other chronic or acute conditions or diseases of the respiratory tract.

So-called inhalers are used for inhalation of drugs. The most frequently used inhalers are pressurized metered-dose inhalers (pMDIs) and dry powder inhalers (DPIs). pMDIs were developed to supply a precise amount or dose of a drug in the form of a cloud of aerosol droplets to the lungs of the patient when the latter inhales. Dry powder inhalers are made such that when the patient inhales they supply a metered amount of dry pulverized particles to the lungs.

An alternative inhaler is shown e.g., in International Patent Application Publication WO 2008/151796 A1 and corresponding U.S. Patent Application Publication 2008/0314380. This inhaler delivers a metered dose of medication as a slow-moving, soft mist through a nozzle system without use of any propellant.

The effectiveness of drugs which are to be inhaled depends largely on the way the inhaler is used by the patient. Optimally, the correct amount of the drug travels to the desired regions of the lungs at the correct instant of time. Otherwise, the therapeutic effect is reduced and/or the risk of contrary effects is increased.

The literature contains numerous instances substantiating that many patients incorrectly use inhalers. Instruction of the patient with respect to a correct inhalation technique can improve the use of inhalers. In addition to written and oral instructions, practical exercises are helpful for this purpose.

Since inhalation generally proceeds subconsciously and develops over the course of a lifetime, it is however especially difficult for a patient to change his/her manner of inhaling in order to increase the effectiveness of a drug which is to be inhaled. Rather, it is known that many patients again use suboptimum inhalation even a short time after instruction. Therefore, repeated, preferably regular practicing (training) of inhalation and checking of it are recommended.

Inhalation training systems were developed for this purpose. Known inhalation training systems differ, among others, with respect to the inhalation model for which the patient is to be trained, with respect to the type of feedback to the patient (for example, acoustically or visually), with respect to the measured variable (for example inhaled volume, volumetric flow or flow rate or mass flow which is produced during inhalation, velocity of the inhaled particles during the inhalation process), with respect to sensors and actuators (for example mechanical, magnetic or electronic) and with respect to size, handling and costs. Some inhalation training systems use inhalers which are available on the market, while other inhalation training systems copy or emulate inhalers or parts of them.

European Patent Application Publication EP 1 993 642 A1 and corresponding U.S. Patent Application Publication 2009/0308387, which form the starting point of this invention, show an inhalation training device for practicing of an inhalation process of a patient. The known inhalation training device comprises a housing that is attachable to and detachable from a mouthpiece of an inhaler designed to provide a drug to the patient and a microphone adapted to measure the airflow occurring in the mouthpiece of the inhaler during an inhalation process of the patient. The known inhalation training device may further comprise data communication means for communication with, e.g., a computer or a device adapted to forward information from a monitoring device to a doctor or other person for analysis and evaluation.

SUMMARY OF THE INVENTION

A primary object of the present invention is to provide an inhalation training device and an inhalation training system that enables effective, simple, reliable, comfortable and/or cost-efficient training of an inhalation process of a patient and/or a simple, cost-efficient, robust and/or regulatory compliant structure and/or a precise measurement of a flow generated by the patient during training and/or a patient-friendly real-time feedback.

The above object is achieved by an inhalation training device and an inhalation training system as described herein.

According to one aspect of this invention, the housing of the inhalation training device is formed of two housing parts snap-clicked together during assembly of the housing. The two housing parts are two simple mechanical parts designed to fit over the mouthpiece of the inhaler. Thus, a robust and cost-efficient unit is created that sits firmly over the mouthpiece, with shortest possible tolerance chain thereby ensuring best possible performance with regards to precise microphone position, with regards to minimal leakage between the mouthpiece of the inhaler and the housing of the inhalation training device thereby supporting the measuring accuracy and finally with regards to mechanical stability. Furthermore, the housing has adequate space inside to contain and protect the microphone, further electronics and cables.

The inhalation training device in accordance with the invention enables effective, comfortable and reliable practicing of an inhalation process.

Preferably, both housing parts are made of molded plastic, in particular acrylonitrile butadiene styrene (ABS), with a smoothed surface. This embodiment enables a cost-efficient structure and a reduction of handling noise caused by the patient practicing an inhalation process, e.g., by sliding or scratching with his fingers over the inhalation training device. Therefore, this embodiment enables higher measurement accuracy.

The measurement accuracy can be increased further by coating both housing parts at least partially with a low-friction layer, in particular glossy chrome. It was found that as much as 15 dB of friction noise difference may exist between a smooth ABS surface and the same surface coated with glossy chrome.

Preferably, the housing comprises molded parting lines for sealed fit with the mouthpiece of the inhaler. This embodiment enables a reliable training of an inhalation process, a robust structure and a precise flow measurement.

According to another aspect of this invention, the microphone is positioned in the housing, outside the mouthpiece of the inhaler and near an air-vent of the mouthpiece of the inhaler, when the inhalation training device is attached to the mouthpiece of the inhaler. This enables a precise flow measurement without any need of intervention within the function of the inhaler and without the need of changing the design of the inhaler. This embodiment does not change the aerodynamic behavior of the flow path of the inhaler. In that manner, the medical compliance of the inhaler is not affected by the presence (or absence) of the inhalation training device.

Preferably, the housing comprises a pad and/or a sleeve around the microphone, in particular made of foam plastic or soft silicone. Thus, insulation of the microphone is improved and vibrations coupling from the inhalation training device into the microphone are reduced. This will further reduce handling noise and improve flow measurement accuracy.

Preferably, the microphone is an electret microphone.

Preferably, the microphone is adapted to measure the noise of the airflow through the air-vent of the mouthpiece of the inhaler. It is well known from acoustics that sound travels well in most solid materials. When a patient inhales using the inhaler, the flow path within the inhaler creates a characteristic flow noise sound depending on flow rate and turbulences. Some of this sound is transmitted through the solid structure of the inhaler. As losses in the solid material are small, it is in principle possible to detect the sound anywhere on the inhaler surface. The preferred embodiment of measuring the noise of the airflow through the air-vent of the mouthpiece of the inhaler enables an effective and reliable training and a precise flow measurement during training.

Preferably, the microphone exhibits directionality, in particular a cardioid, super-cardioid, hyper-cardioid or a bi-directional characteristic. The directional microphone characteristic allows for the microphone itself cancelling out signals that originate from outside the mouthpiece of the inhaler, however not affecting sounds that originate from within. Thus, influence from ambient noise during training can be reduced and flow measurement accuracy can be increased.

Preferably, the inhalation training device provides an interface to an electronic device. The electronic device preferably is a portable communications device capable of capturing, transmitting and/or outputting information and which can be easily transported by an individual. Typical applications of portable communications devices are telephony, data transmission, games, text processing, table processing, image processing, photography and music playback. Typical examples of portable communications devices are mobile phones, smartphones, tablet PCs, handhelds and PDAs.

This embodiment enables exploitation of the functionality of the electronic device, especially for processing and/or evaluation of the signal measured by the microphone of the inhalation training device and/or for feedback to the patient and/or a third party in a simple, intuitive, reliable and cost-efficient manner. At the same time, this embodiment enables expansion of the functionality of the electronic device in a simple and cost-efficient manner with respect to practicing of an inhalation process of a patient.

As a result of the popularity of portable communications devices, access to inhalation training can also be provided to patients who would not like to buy a special electronic device only for inhalation training. Since the owners of portable communications devices are accustomed to their handling, the embodiment in accordance with the invention also enables easier and faster learning of an optimum inhalation process. Since many individuals continually carry a portable communications device, the embodiment in accordance with the invention can also lead to more frequent, possibly regular inhalation training. Furthermore, the embodiment in accordance with the invention increases the ease of operation and the portability of inhalation training.

In particular, the interface to the electronic device is realized by means of an audio jack, especially a 3.5 mm TRRS headset connector. Audio jack is a generic term for a family of connectors typically used for analog audio signals. An audio jack typically has a cylindrical shape, typically with two, three or four contacts. Four-contact versions are known as TRRS connectors, where T stands for "tip", R stands for "ring" and S stands for "sleeve". Modern audio jacks are available in three standard sizes, i.e. 6.35 mm, 3.5 mm and 2.5 mm.

As the 3.5 mm TRRS headset connector is the globally most common connector for portable communications devices, the proposed embodiment ensures that the inhalation training device is compatible to a wide range of portable communication devices and is required only in one variant. Thus, the proposed embodiment enables a comfortable and cost-efficient training of an inhalation process of a patient and a patient-friendly real-time feedback.

However, even if manufacturers have agreed on the physical format for the 3.5 mm TRRS headset connector, they disagree on various details associated with the electronic interfacing. One of the most fundamental differences is the polarity of the microphone connections, which, e.g., differ between the family of Apple devices compared to most other manufacturers, e.g., Samsung, HTC, LG, Sony, Motorola, Microsoft, Blackberry and Nokia. The typical connection schemes is given by the following table.

|  | Apple | Other manufacturers |
| --- | --- | --- |
| Tip | Left audio | Left audio |
| Ring | Right audio | Right audio |
| Ring | Ground | Microphone |
| Sleeve | Microphone | Ground |

Preferably, the inhalation training device comprises electronics configured to swap the electric connection to the microphone and to ground in dependence of the connection scheme of the TRRS headset connector. In particular, the differing polarity of the microphone connections are handled automatically using analog electronic switches placed in the connection between the microphone and the TRRS headset connector. Especially, the microphone bias voltage (i.e., the positive voltage on the microphone connection) is used directly to select the relevant switching and both the microphone and the ground connections will hence be swapped as necessary. Such analog switching provides excellent audio properties and very limited resistance down to well below 1 Ohm.

Besides the polarity of the microphone connections there also exist minor differences in how and when a specific portable communications device recognizes that an external connection is established, related to the impedance level between the microphone and ground connectors.

Preferably, the inhalation training device comprises electronics configured to adjust the frequency range in which the microphone operates as a function of the analog front-end sensitivity of the electronic device. The flow-induced noise measured by the microphone of the inhalation training device is to be analyzed to assess the air-flow and typically this means to convert the sound pressure level (e.g., in selected frequency bands) to a sound pressure level and then use established correlation patterns between noise and flow to determine the appropriate flow level. This however assumes well-specified audio properties of the electronic device, in particular the analog front-end sensitivity but also linearity and (for wide band signals) frequency range and linearity.

In order to handle speech in high quality, electronic devices typically filter a frequency range from 200 Hz to 20000 Hz. From the perspective of the inhalation training device, turbulent flow noise will generally have a wide-band noise profile covering at least the frequencies from 100 Hz to 10000 Hz, but typically the flow signal is carried well within narrow bands, e.g., 500 Hz to 1000 Hz (dependent on the inhaler type among others). The preferred embodiment of the inhalation training device therefore allows for adjusting the frequency range in which the microphone operates depending on the audio properties of the electronic device, in particular, its analog front-end sensitivity.

With respect to the amplitude linearity, the inhalation training device preferably targets the typical speech range of amplitudes in order to be less prone to potential (unknown) compression. The electronics of the inhalation training device is, however, tunable to stay in the linear region of the most restrictive electronic device thereby ensuring an adequate uniform electronics interface to all selected electronic devices.

Preferably, the inhalation training device comprises electronics configured to generate a reference tone during training. Thus, the reference tone accompanies the microphone signal to at all times make available a known reference. This reference tone can be realized by implementing a precise oscillator of a well-defined frequency (e.g., 10 kHz) and amplitude into the electronics of the inhalation training device and mixing the reference tone into the microphone signal.

Preferably, the oscillator for the reference tone is build up around a low voltage operational amplifier and a precision voltage controller which defines an amplitude of 1.2 V.

Preferably, the housing of the inhalation training device is designed to prevent wrong positioning (e.g., up/down and/or right/left rotation from correct position) of the housing when being attached to the mouthpiece of the inhaler.

According to another aspect of this invention, the housing is designed to prevent drug release and/or dispensing of any fluid during training. In particular, parts of the housing of the inhalation device cover the drug release actuator of the inhaler when the inhalation training device is attached to the mouthpiece of the inhaler. This embodiment ensures that the inhalation training device complies with regulatory requirements, e.g., the EU Medical Device Directive (MDD/93/42/EEC) and the US Medical Device guidelines (FDA 21 CFR Part 820).

Another aspect of the present invention relates to an inhalation training system for practicing of an inhalation process of a patient. According to this aspect, the inhalation training system comprises an inhalation training device according to one or more of the preceding aspects, an inhaler and an electronic device configured for evaluation of a signal received from the inhalation training device and for visual and/or audio feedback to the patient.

This inhalation training system enables an effective, simple, reliable, comfortable and cost-efficient training of an inhalation process of a patient and a precise measurement of a flow generated by the patient during training and a patient-friendly real-time feedback.

Preferably, the inhalation training system is configured to detect the presence of exhalation of the patient during training. When the patient should accidentally exhale into the mouthpiece of the inhaler during training, this can wrongfully reinforce an incorrect or inefficient patient behavior. Therefore, detecting the presence of exhalation of the patient during training enables an effective training of an inhalation process of the patient.

Measurements of either inhalation or exhalation flow and then extraction of the frequency spectra for each individual flow level, separately for inhalation and exhalation, showed that generally the inhalation flow produces flatter spectral responses compared to exhalation flow. This means that when calculating the ratio between the low frequency versus high frequency energy contents then exhalation produces a greater ratio than would inhalation. The inhalation training system exploits this relationship by defining a suitable threshold separating these two frequency clusters. For example, the low frequency signal content is assessed using as a 300 Hz filter whereas the high frequency signal content is assessed using a 7000 Hz filter and a threshold of 70 has been identified to provide good separation between inhalation and exhalation for low flow rates of approximately 10-30 l/min.

Towards higher flow rates, however, the spectral curves for inhalation and exhalation respectively tend to look more and more alike meaning that this separation will not have sensitivity for high flow rates. To handle this situation, another cue is employed based on another characteristic tendency for the above flow sound spectra, namely that the exhalation sound spectra tend to reach higher levels in the low frequency region than does the complementary inhalation sound spectra. Based on this observation, an additional indicator for presence of exhalation flow is the low frequency signal energy. Preferably, the inhalation training system decides on having detected an exhalation if the low frequency signal energy exceeds a threshold of 7. This threshold provides adequate separation between the inhalation and exhalation for high flow rates of approximately 50-90 l/min.

The definition of the preferred thresholds has been made with a clear ambition to have a high degree of detection specificity, i.e., the inhalation training system should not give a warning of exhalation while the patient is actually inhaling correctly.

Preferably, the electronic device is configured to detect the presence of a characteristic voice signal in the signal received from the inhalation training device. Human voice typically does not have a flat sound spectrum but rather consist of an equally spaced train of peaks and valleys starting with the lowest formant frequency. The electronic device can be configured to cease flow evaluation temporarily if the signal received from the inhalation training device is dominated by such a characteristic voice signal or spectrum. Thus, robustness against the influence of voice is improved.

Preferably, the electronic device is configured to detect the presence of the inhalation training device and/or a specific type of the inhaler, in particular by means of a reference tone generated by the inhalation training device during training. For this purpose, the reference tone generated by the inhalation training device as described above can be utilized, especially for automated robust detection that an inhalation training device as claimed has been plugged via the interface (3.5 mm TRRS headset connector) into the electronic device. The electronic device can be configured to not provide any feedback related to flow detection if this is not the case.

The electronic device preferably is a portable communications device capable of capturing, transmitting and/or outputting information and which can be easily transported by an individual. Typical examples of portable communications devices are mobile phones, smartphones, tablet PCs, handhelds and PDAs. The electronic device within the scope of this invention is a device which is separate or independent of the inhalation training device.

Preferably, the electronic device is designed for storage, output and/or interactive feedback of a measured, processed and/or evaluated signal to the patient and/or a third party. In particular, the electronic device has a device for acoustic feedback of the evaluation, for example, a speaker, and/or for visual feedback of the evaluation, for example a screen.

The electronic device can, in particular, provide instructions for correct inhalation and/or advice for optimization. For more effective training of the patient the electronic device can additionally display pictures and/or videos which illustrate an optimum inhalation process.

The term "interactivity" designates the properties of making available to the patient intervention and control possibilities for individualized learning. To do this, for example, the choice and the type of representation of information can be adapted to prior knowledge, the interests and needs of the patient or can be manipulated by him. Solely making available information does not constitute interactive feedback for the purposes of this invention.

Preferably, the electronic device is designed for wireless transmission of a measured, processed and/or evaluated signal to another electronic device. In this way, the signal can be transmitted, for example, to a physician who on this basis can prepare a diagnosis and/or can give advice for improving the inhalation process.

Preferably, the electronic device is designed or can be used for practicing an effective inhalation time $T_{in,\,eff}$ which is as optimal as possible. In this way, the patient is enabled to achieve an effective inhalation time that is as optimal as possible. The effective inhalation time is the time during an inhalation of an inhalation training process, especially the time of simulated inspiration, in which the delivery of an amount or dose of a drug is simulated. In particular, the effective inhalation time is the portion of time in which the inhalation and the simulated delivery of the dose of drug overlap.

Based on the effective inhalation time an inhaled dose of drug (iDoD) can be estimated. This applies especially when the drug is typically delivered at a constant rate. The inhaled dose of drug can be given as a percentage of the delivered dose of drug. The effective inhalation time and the inhaled dose of drug are indicative with respect to the quality of the inhalation process.

To practice the effective inhalation time, the electronic device is preferably designed for determination of the effective inhalation time. To determine the effective inhalation time, the electronic device can determine a delivery time or spray time. The delivery time or spray time is the time during which a delivery of a dose of drug is simulated. The end of delivery is preferably fixed by a fixed delivery duration or spray duration (SDur). Preferably, the effective inhalation time is given in a percentage of the spray duration.

In one preferred embodiment, the effective inhalation time is 0% when the delivery time is outside the time of the inhalation process or of inhalation ($T_{in}$), i.e., when the delivery time has passed before the start of the inhalation process. In this embodiment, the effective inhalation time is 100% when the delivery time is completely within the time of the inhalation process.

If the delivery begins before the start of the inhalation process and the delivery ends after the end of the inhalation process, the effective inhalation time is determined preferably according to the following formula:

$$T_{in,eff}[\%]=T_{in}*100/SDur$$

If the delivery starts after the start and before the end of the inhalation process and the delivery ends after the end of the inhalation process, the effective inhalation process is preferably determined according to the following formula:

$$T_{in,eff}[\%]=(1-(\Delta+SDur-T_{in})/SDur)*100,$$

$\Delta$ being the difference between the start of the delivery and start of the inhalation process, i.e., $\Delta$ has a positive value when the delivery starts after the start of the inhalation process and $\Delta$ is a negative value when the delivery starts before the start of the inhalation process.

If the delivery starts before the beginning of the inhalation process and the delivery ends after the start and before the end of the inhalation process, the effective inhalation process is preferably determined according to the following formula:

$$T_{in,eff}[\%]=(\Delta+SDur)/SDur*100,$$

$\Delta$ being the difference between the start of the delivery and start of the inhalation process.

In particular, when determining the effective inhalation time solely the inspiration times can be considered as the inhalation time $T_{in}$. Therefore, if inspiration is interrupted by holding the breath or expiration, these times are preferably subtracted from the inhalation time.

Alternatively or in addition, the electronic device can be designed for determination or estimation of a volumetric flow or flow rate which has been generated in the inhalation process and/or a flow velocity generated here. These two physical quantities are highly indicative with respect to the quality of the inhalation process.

The electronic device can also be designed for determination or estimation of the flow velocity. It has been found that depending on where the drug is to be deposited (throat, lungs), the velocity of the inhaled drug must be different. Thus, the flow velocity may be of interest in the determination whether the inhalation was correct. The electronic device can also be designed for determination or estimation of the time during which the flow was within a certain flow velocity interval or above a certain lower limit, again to ensure that the inhalation was correct or sufficient.

Preferably, practicing of inhalation is carried out with support by software which is matched to the electronic device and can be ordered, in particular, via an online portal and installed. Typically, this software is called an "App". The use of an App improves the flexibility and ease of operation.

The App can be used, for example, for processing and interpretation of the measured signal and for feedback to the patient and/or a third party. To do this, the App can be made available or executed using an information storage medium. The information storage medium is preferably made for use in a portable communications device, especially optimized with respect to the space requirement, energy consumption, reliability and data transmission rate.

Preferred steps of the App are described below.

In the preferred steps of the App, the App is started in a first step. In a later step a graphic user interface (GUI) is initiated and preferably displayed on a screen of the electronic device. In particular, a visual start indication or visual trigger indication is also displayed.

In another step a loop function is started using which the GUI is updated in order to display for example altered contents of the GUI.

Preferably, the start indication or trigger indication is evaluated using the App. In particular, an input of the user or patient, quite especially the actuation of the start indication or of the trigger indication by the user or patient, is monitored. The monitoring of the input leads preferably to a decision whether the start indication or trigger indication has been actuated. If it is decided that an actuation of the start indication or trigger indication has taken place, preferably two parallel branches are followed by the App.

On the one hand, in a first branch, it is preferably monitored whether a visual stop indication (especially on the screen) is actuated. This monitoring leads preferably to a decision whether the stop indication has been actuated. On the other hand, in a second branch parallel to the monitoring of the stop indication an electrical signal value or several electrical signal values of the inhalation training device is or are read out. Preferably the App or the electronic device induces processing of the electrical signal values, especially digitization and storage of the electrical signal values.

In another step, in the second branch, a volumetric flow or flow rate which has been produced in the inhalation process is determined and/or a flow rate profile is prepared using the App or the electronic device.

Within the second branch, preferably, the starting of an inhalation process is monitored by the App or the electronic device. Monitoring leads preferably to a decision whether the inhalation process has been started. Here the App or the electronic device is preferably designed such that an actuation of the trigger indication is interpreted as starting of an inhalation process; this leads to the decision that the inhalation process has started.

If it is decided that an inhalation process has started, on the one hand, preferably a starting time is determined by the App or the electronic device. In addition, preferably further time values can be determined by the App or the electronic device via time keepers.

If it is decided that an inhalation process has started, on the other hand, preferably the ending of the inhalation process is monitored by the App or the electronic device. The monitoring leads preferably to a decision whether the inhalation process has ended. Here the App or the electronic device is preferably designed such that a repeated actuation of the trigger indication or an actuation of the ending indication (especially on the screen) is interpreted as ending of the inhalation process; this leads to the decision that the inhalation process has ended.

If it is decided that the inhalation process has ended, preferably a stop time is determined by the App or the electronic device.

If the monitoring of the ending of the inhalation process after passage of a defined time (for example 20 seconds) beginning from a fixed start of the inhalation process does not lead to a decision that the inhalation process has ended, preferably ending or abort of the App or the sequence takes place. If an abort is ascertained by the App or the electronic device, the App is ended. For example, the GUI can be ended so that it is no longer displayed. Furthermore, time values can be reset and/or memories can be released.

If a stop time is determined, a time keeper is preferably determined by the App or the electronic device. Moreover, preferably an evaluation of the electrical signal values is undertaken. Thus, for example using the App or the electronic device an effective inhalation time and/or inhaled dose of drug can be determined, as already described.

Results of the evaluation can be displayed on the GUI, for which the GUI can be updated.

Furthermore, the App or the electronic device is preferably made such that feedback to the patient and/or a third party takes place, especially an alarm indication is output, when the flow rate which has been determined by the App or the electronic device rises above a value of roughly 40 liters per minute and/or drops below a value of roughly 20 liters per minute.

If it is decided that the stop indication has been actuated, preferably the GUI is updated and/or an abort is checked. The App can also be ended or aborted by actuating an abort indication (especially on the screen).

Another aspect of this invention relates to an information storage medium, especially for a portable communications device. Instructions are stored on the information storage medium in accordance with the invention and when they are executed by a processor they preferably cause the following steps to be carried out:
  initialization of a graphic user interface,
  read-out of an electrical signal value of an inhalation training device as described above,
  digitization and/or storage of the electrical signal value and
  determination of an effective inhalation time and/or inhaled dose of drug.

The information storage medium in accordance with the invention enables effective, simple, reliable and cost-efficient practicing of a patient inhalation process.

Before describing the drawings, some terms are defined below.

The term "inhalation process" in accordance with the invention preferably comprises inhalation of the patient, wherein inhalation can be interrupted over a short time interval, therefore it can comprise the inhalation breaths in rapid succession. Furthermore, an inhalation process can also comprise stopping of the air or of the inhalation and/or the exhalation and/or a coughing of the patient.

The term "patient" in accordance with the invention designates preferably an individual who must and/or would like to use an inhaler, especially an individual who is suffering from a disease of the respiratory tract, quite especially from asthma or a chronically obstructive pulmonary disease, and is treating the disease by means of an inhaler.

The terms "flow" and "airflow" for the purposes of this invention are defined as a measurable flowing movement of air with or without turbulence.

The above aspects and features of this invention and the aspects and features of the invention which follow from the further description and the claims can be implemented independently of one another, but also in any combination.

Other advantages, features, properties and aspects of this invention will become apparent from the following description of preferred embodiments with reference to the drawings.

DETAILED DESCRIPTION OF THE INVENTION

In the figures, the same reference numbers are used for the same or similar parts, corresponding properties and advantages being achieved even if a repeated description is omitted.

Figure 1:
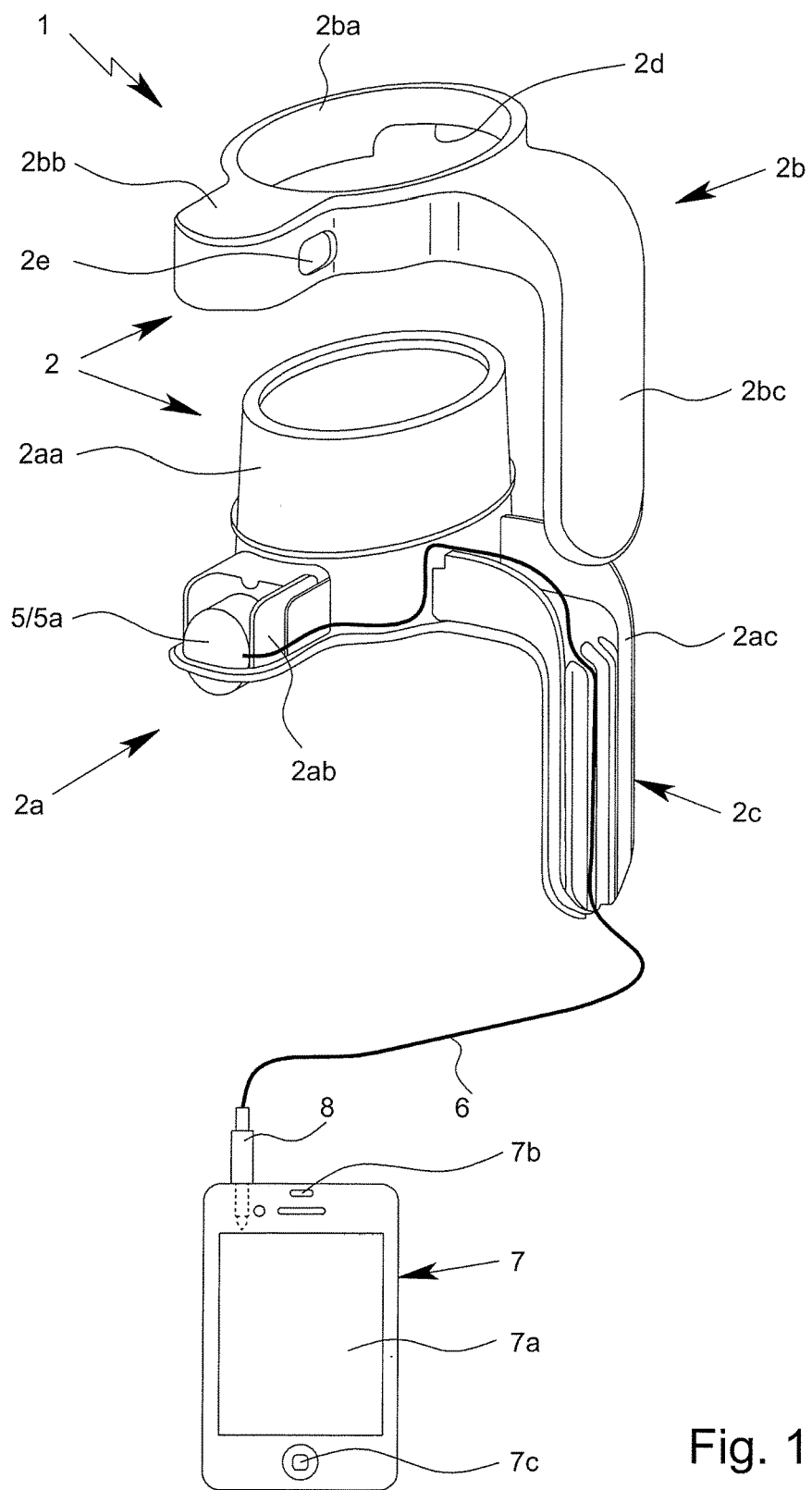
FIG. 1 schematically shows a perspective view of a preferred embodiment of an inhalation training device according to the present invention, in a state prior to its final assembly and together with a smartphone.

FIG. 1 schematically shows a perspective view of a preferred embodiment of an inhalation training device 1 according to the present invention in a state prior to its final assembly.

The inhalation training device 1 is or can be used for practicing an inhalation process of a patient who is not shown.

The inhalation training device 1 comprises a housing 2 attachable to and preferably detachable from a mouthpiece 3 or any other component of an inhaler 4, in particular a so-called RESPIMAT® inhaler as shown, e.g., in WO 2008/151796 A1 and corresponding U.S. Patent Application Publication 2008/0314380. The inhaler 4 is designed to provide a drug to a patient.

In the preferred embodiment, the inhalation training device 1 only works in combination with a specified or definite inhaler 4, such as the RESPIMAT® inhaler 4. In particular, the inhalation training device 1 only works as intended when mounted over or to the inhaler 4, in particular its mouthpiece 3.

The inhalation training device 1 comprises a microphone 5 adapted to measure the airflow occurring in or into the mouthpiece 3 during an inhalation process of the patient.

In the preferred embodiment, the microphone 5 is an electret microphone.

Figure 3:
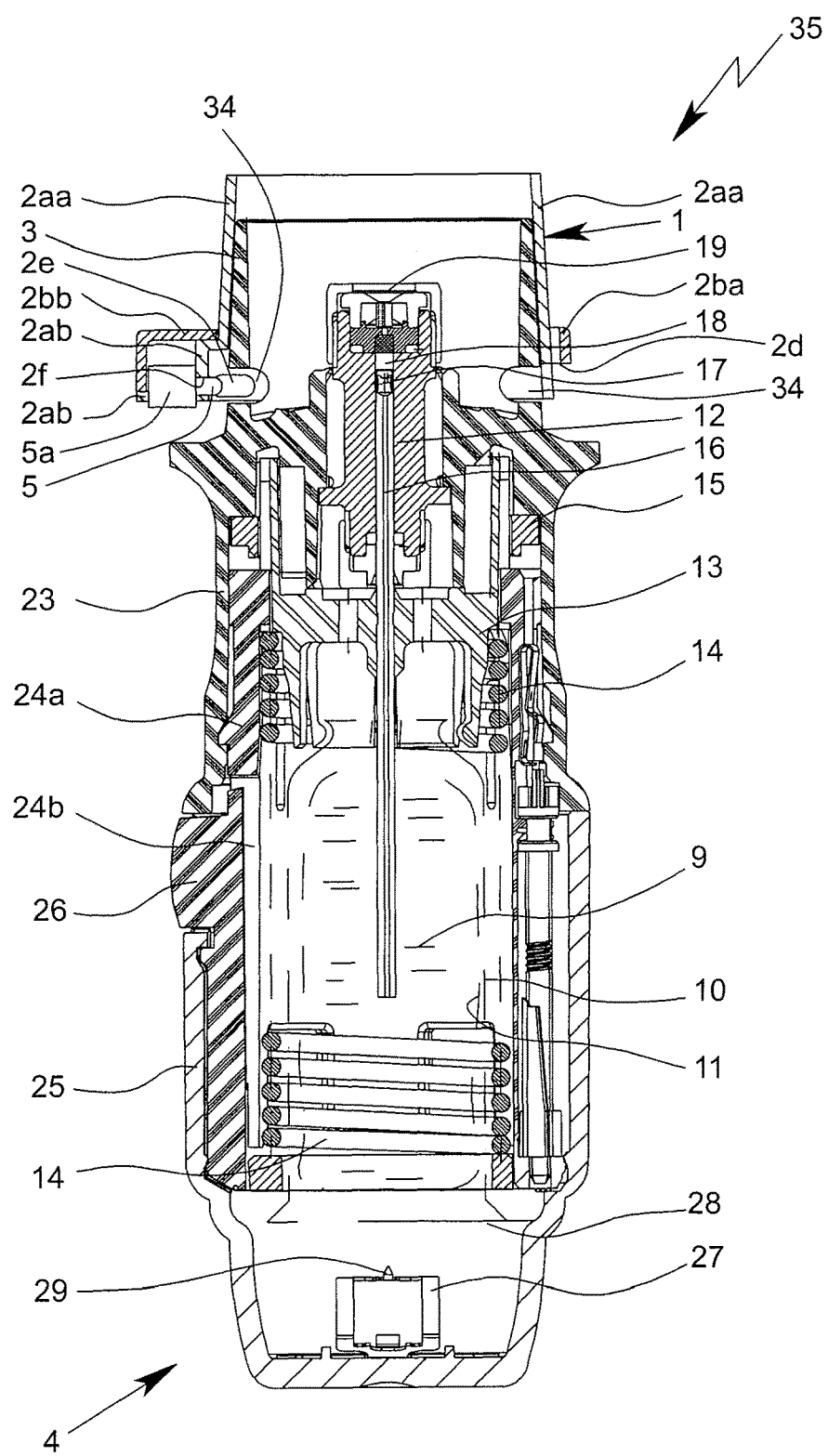
FIG. 3 schematically shows a section through an inhaler with the inhalation training device attached to a mouthpiece of the inhaler which is in a relaxed state.

Preferably, the inhalation training device 1 or microphone 5 is adapted to measure the noise of the airflow through an air-vent, such as an opening 34 shown in FIG. 3, of the inhaler 4 or the mouthpiece 3.

Preferably, the housing 2 of the inhalation training device 1 comprises or consists of two housing parts 2a, 2b, preferably a lower housing part 2a and an upper housing part 2b.

Preferably the housing 2 or lower housing part 2a has a holding or cylindrical section 2aa, which has preferably the shape of a hollow oblique cylinder with an elliptic base. The shape of the section 2aa is preferably similar or adapted to the shape of the mouthpiece 3 of the inhaler 4, preferably so that the section 2aa can be pushed onto the mouthpiece 3.

In particular, the circumference of the cylindrical section 2aa of the lower housing part 2a is greater than the circumference of the mouthpiece 3 of the inhaler 4.

The section 2aa or lower housing part 2a comprises preferably an outward or essentially radial protrusion 2ab.

The lower housing part 2a preferably comprises a finger or cover 2ac protruding from or connected to the cylindrical section 2aa. Preferably, the finger 2ac is spaced from the protrusion 2ab of the lower housing part 2a along the circumference of the cylindrical section 2aa.

The upper housing part 2b comprises preferably a cylindrical section 2ba, which has preferably the shape of a hollow oblique cylinder with an elliptic base. The circumference of the cylindrical section 2ba of the upper housing part 2b is preferably greater than the circumference of the cylindrical section 2aa of the lower housing part 2a. The height of the cylindrical section 2ba of the upper housing part 2b is preferably smaller than the height of the cylindrical section 2aa of the lower housing part 2a. The cylindrical section 2ba of the upper housing part 2b comprises preferably an outward protrusion 2bb. The upper housing part 2b comprises preferably a finger or cover 2bc. Preferably, the finger or cover 2bc protrudes from the cylindrical section 2ba of the upper housing part 2b and/or is spaced from the protrusion 2bb of the upper housing part 2b along the circumference of the cylindrical section 2ba of the upper housing part 2b.

During assembly of the housing 2, the microphone 5 is mounted in the protrusion 2ac of the lower housing part 2a and an audio cable 6 connected to the microphone 5 is lead out of the protrusion 2ac of the lower housing part 2a alongside the cylindrical section 2aa and the cover 2ac of the lower housing part 2a. Furthermore, the upper housing part 2b is put over the lower housing part 2a and both housing parts 2a, 2b are snap-clicked together such that the cylindrical section 2ba of the upper housing part 2b surrounds the cylindrical section 2aa of the lower housing part 2a and that the protrusion 2bb of the upper housing part 2b covers the protrusion 2ab of the lower housing part 2a and that the cover 2bc of the upper housing part 2b covers the cover 2ac of the lower housing part 2a.

Preferably, the housing parts 2a and 2b are connected with each other by snap-fit and/or form-fit.

Preferably, the housing 2 holds or receives the microphone 5 and/or an associated cable 6.

Preferably, the microphone 5 is received between the housing parts 2a and 2b.

Preferably, the cable 6 is received and/or guided between the housing parts 2a and 2b and/or the sections 2ac and 2bc.

The inhalation training device 1 or housing 2 comprises preferably a blocking device 2c for blocking actuation of the inhaler 4. Preferably, the blocking device 2c is formed by the section 2ac and/or 2bc.

Figure 4:
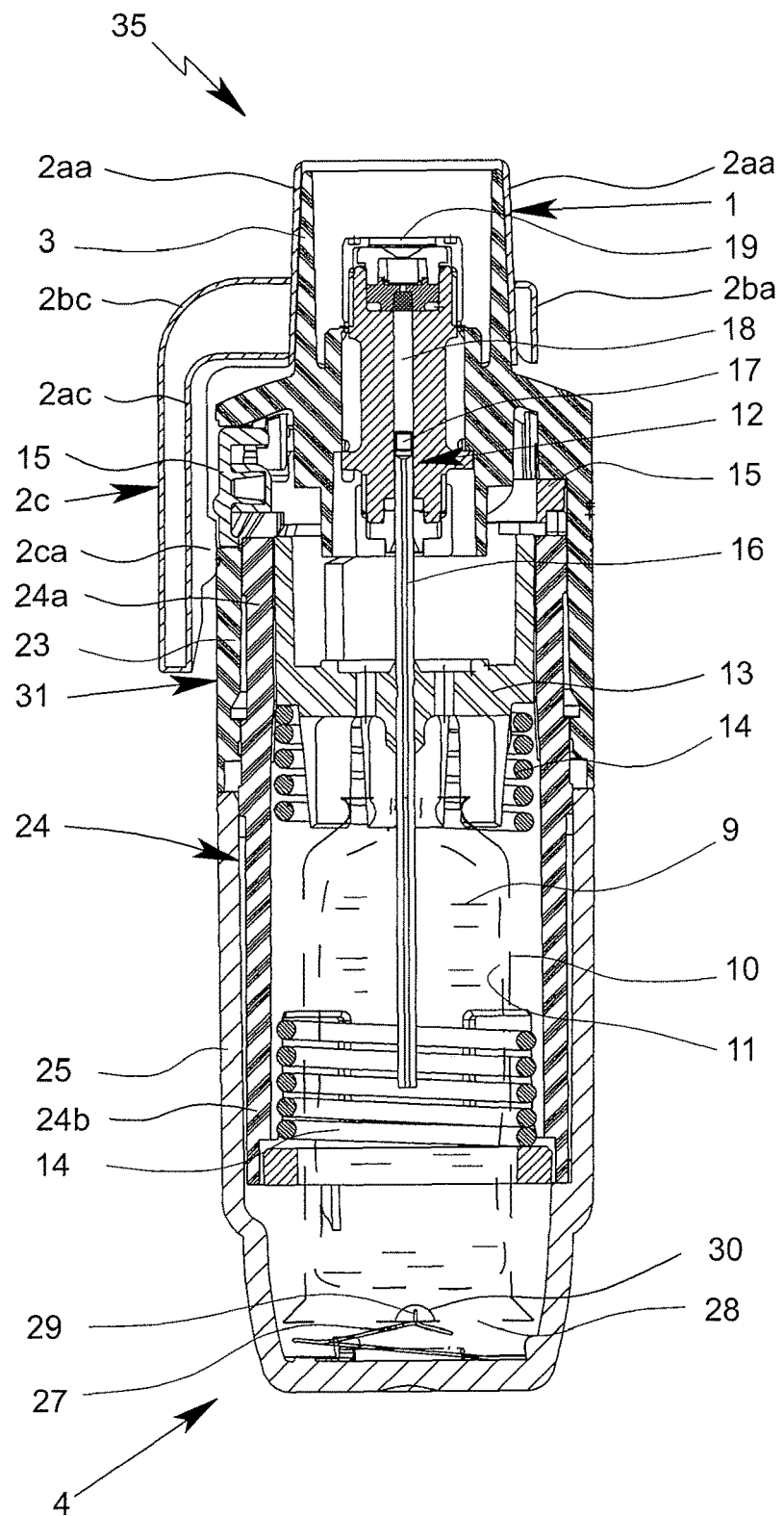
FIG. 4 schematically shows the inhaler of FIG. 3 axially rotated about 90° in a tensioned state.
Figure 5:
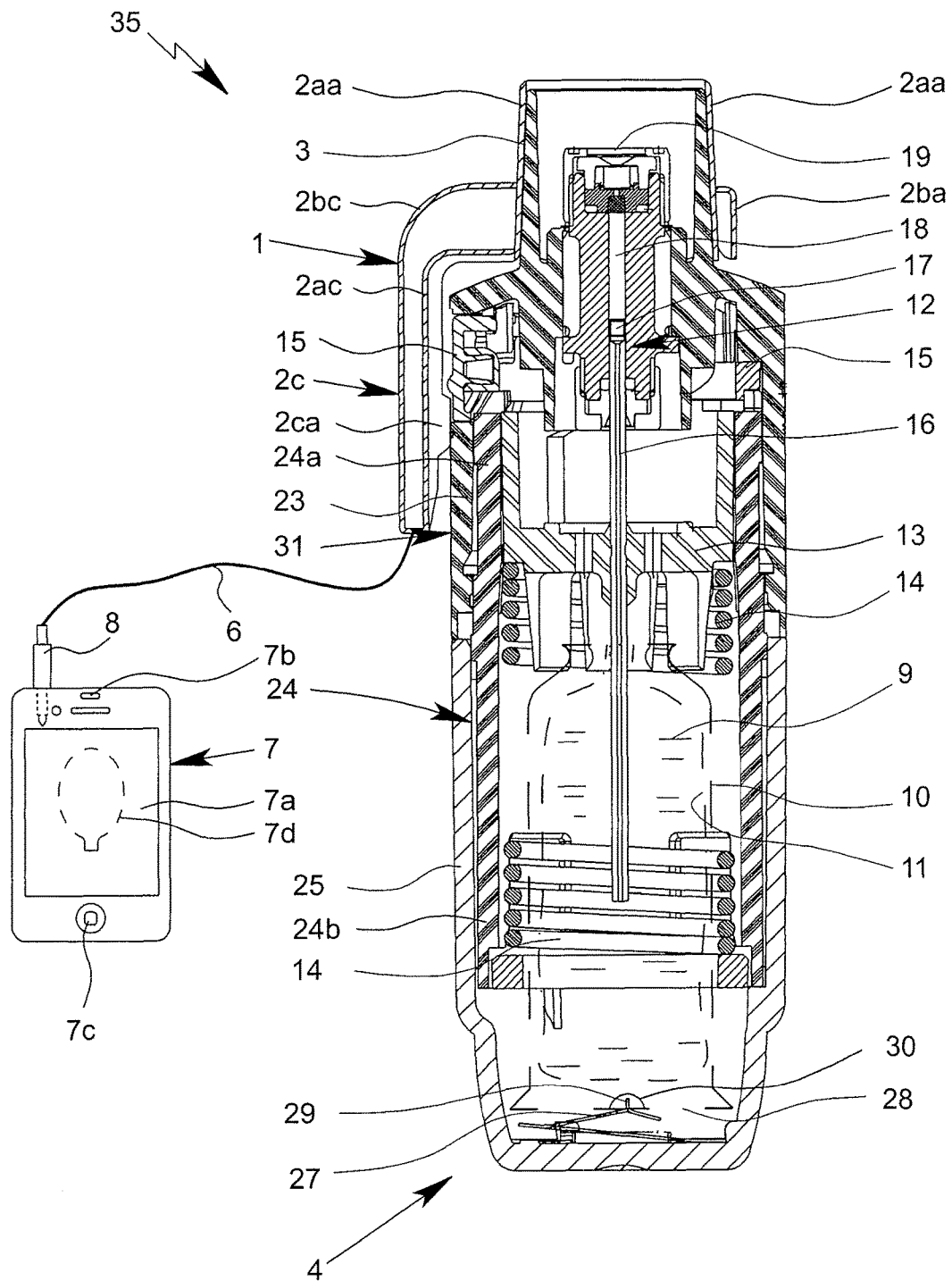
FIG. 5 schematically shows a perspective view of an inhalation training system according to the present invention.

Preferably, the blocking device 2c is formed or realized as a finger covering a blocking element 15 of the inhaler 4 as schematically shown in FIGS. 4 and 5.

Preferably, the blocking device 2c and/or sections 2ac, 2bc extend at least partially in axial direction and/or parallel to a longitudinal direction of the inhaler 4 and/or to a longitudinal axis of the housing 2 or holding section 2aa.

The holding section 2aa is adapted to mount the inhalation training device 1 or its housing 2 to the associated inhaler 4, in particular to its mouthpiece 3 or any other component. Most preferably, the section 2aa allows a mechanical connection by press-fit to the mouthpiece 3 or the like.

Preferably, the outer contour of the mouthpiece 3 and the inner contour of the section 2aa are slightly tapered towards the free end and adapted so that the desired clamping can be achieved when the section 2aa is pushed onto the mouthpiece 3. However, other forms and/or constructional solutions are possible.

Figure 2:
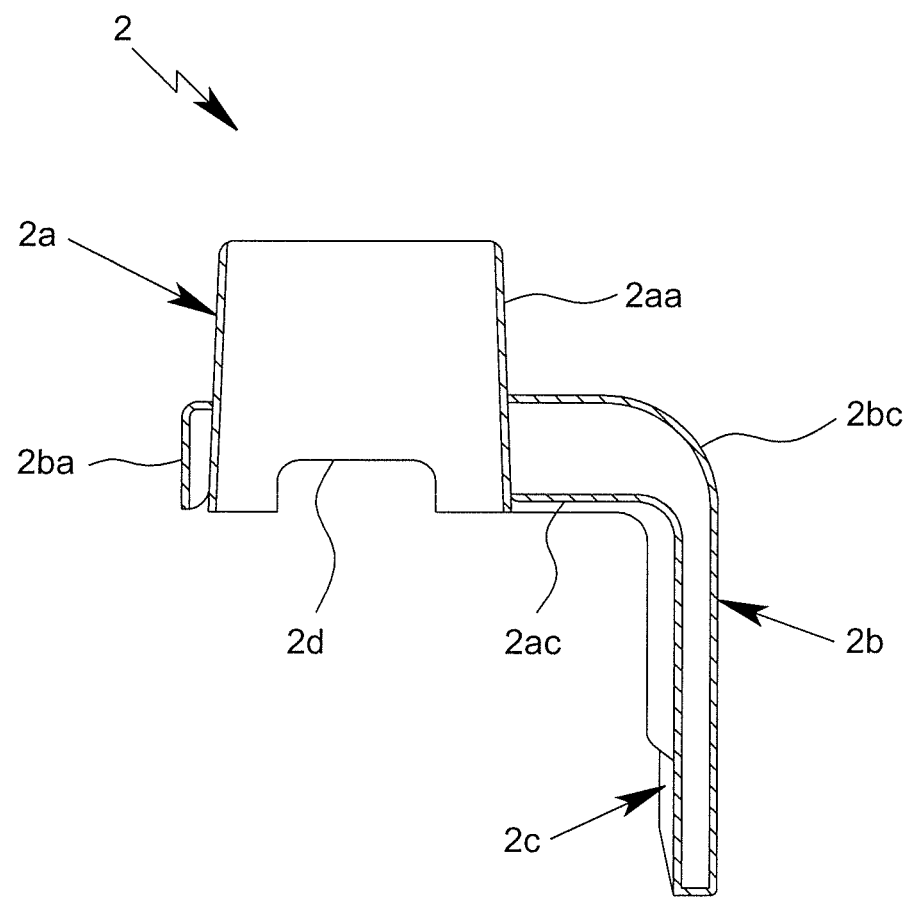
FIG. 2 schematically shows a section through a housing of the inhalation training device after final assembly of the housing.

FIG. 2 schematically shows a section through the housing 2 of the inhalation training device 1 after final assembly of the housing 2, but without microphone 5, cable 6, and the like.

Both housing parts 2a, 2b are made preferably of molded plastic with a smoothed surface. Thus, handling noise caused by the patient practicing an inhalation process, e.g., by sliding or scratching with his fingers over the inhalation training device 1, is reduced. Therefore, measurement accuracy is increased.

The inhalation training device 1 provides an interface and/or is connectable to an electronic device 7. In the preferred embodiment of FIG. 1, the electronic device 7 is a smartphone.

In the preferred embodiment, the interface and/or connection to the electric device 7 is realized preferably by means of cable 6 and/or a connector 8, such as an audio jack, in particular a 3.5 mm TRRS headset connector or the like.

As the 3.5 mm TRRS headset connector 8 is the globally most common connector for smartphones, the inhalation training device 1 is preferably compatible to a wide range of smartphones and is required only in one variant. This enables a comfortable and cost-efficient training of an inhalation process of a patient and a patient-friendly real-time feedback.

Additionally or alternatively, the inhalation training device 1 can be connected with the electric device 7 wireless, e.g., via Bluetooth.

In the preferred embodiment, the inhalation training device 1 comprises electronics 5a (indicated in FIGS. 1 and 3) configured to process any microphone signal and/or to generate a reference tone during training. Thus, the reference tone accompanies the signal of the microphone 5 at all times and makes available a known reference. In particular, this reference tone is realized preferably by implementing a precise oscillator of a well-defined frequency of about 10 kHz and an amplitude of preferably 1.2 V into the electronics 5a of the inhalation training device 1 and mixing the reference tone into the microphone signal.

FIG. 3 schematically shows a section through the inhaler 4 with the inhalation training device 1 attached to the mouthpiece 3 of the inhaler 4. FIG. 4 schematically shows also a section through the inhaler 4 with the inhalation training device 1 attached to the mouthpiece 3 of the inhaler 4, whereas the inhaler 4 and the attached inhalation training device 1 are axially rotated about 90°.

The two housing parts 2a, 2b are designed preferably to exactly fit together and to firmly fit over the mouthpiece 3 of the inhaler 4. This ensures minimal leakage between the mouthpiece 3 of the inhaler 4 and the housing 2 of the inhalation training device 1. Thus, high measurement accuracy and high mechanical stability is achieved. At the same time, the housing 2 has adequate space inside to contain and protect the microphone 5, audio cable 6 and further electronics 5a.

Furthermore, the described design of the housing 2, in particular non-circular cross-section of the section 2aa and the mouthpiece 3, prevents wrong positioning of the housing 2 when being attached to the mouthpiece 3 of the inhaler 4.

In the illustrated and preferred embodiment, the housing 2 is designed such that drug release during training is prevented. In particular, the blocking device 2c or covers 2ac, 2bc of the two housing parts 2a, 2b cover a drug release actuator, such as blocking element 15, of the inhaler 4 when the inhalation training device 1 is attached to the mouthpiece 3 of the inhaler 4.

When the inhalation training device 1 is attached to the mouthpiece 3 of the inhaler 4, the microphone 5 is positioned preferably automatically, outside the mouthpiece 3 of the inhaler 4 and/or near an air-vent or opening 34 of the mouthpiece 3 of the inhaler 4. This enables a precise flow measurement without any need of intervention within the function of the inhaler 4 or fluid flow in the mouthpiece 3 and without the need of changing the design of the inhaler 4. Preferably, the aerodynamic behavior of the flow path of the inhaler 4 is not changed by the inhalation training device 1. In that manner, the medical compliance of the inhaler 4 is not affected by the presence (or absence) of the inhalation training device 1.

Measurements were taken using calibrated TetraTec flow measuring equipment (TetraTec Instruments GmbH, 71144 Steinenbronn, Germany) and comparison was made using a stand-alone inhaler 4 and then the same inhaler 4 where the inhalation training device 1 was mounted over the mouthpiece 3 of the inhaler 4. In both situations the flow resistance was measured for a tube connected to the mouthpiece 3 (not covering the air vents). Measurements showed that airflow is not restricted by the presence of the inhalation training device 1. The flow resistance when using the inhalation training device 1 is unchanged compared to the stand-alone inhaler 4 thereby supporting the requirements to not train patients with another type of inhalation experience.

In the following, the inhaler 4 is described in more detail.

The inhaler 4 is designed to atomize a fluid 9, particularly a highly effective pharmaceutical composition, medicament or the like, diagrammatically shown in a relaxed state (FIG. 3) and in a tensioned state (FIG. 4). The inhaler 4 is constructed, in particular, as a portable inhaler and preferably operates only mechanical and/or without propellant gas.

The inhaler 4 is provided with or comprises an insertable or replaceable container 10 containing the fluid 9. The container 10 thus forms a reservoir for the fluid 9, which is to be nebulized. Preferably, the container 10 contains multiple doses of fluid 9 or active substance in particular sufficient to provide up to 200 dosage units or doses, for example, i.e., to allow up to 200 sprays or applications. A typical container 10, as disclosed in WO 96/06011 A1 and corresponding U.S. Pat. No. 5,833,088, holds, e.g., a volume of about 2 to 20 ml.

It is noted that the dose can vary, in particular depending on the fluid 9 or medicament. The inhaler 4 can be adapted respectively.

Further, the number of doses contained in the container 10 and/or the total volume of the fluid 9 contained in the container 10 can vary depending on the fluid 9 or respective medicament and/or depending on the container 10 and/or depending on the necessary medication or the like.

Preferably, the container 10 can be replaced or exchanged, wherein the number of containers 10, which can be used with the same inhaler 4, is preferably restricted, e.g., to a total number of four or five containers 10.

The container 10 is preferably substantially cylindrical or cartridge-shaped and once the inhaler 4 has been opened the container 10 can be inserted therein preferably from below and changed if desired. It is preferably of rigid construction, the fluid 9 in particular being held in a collapsible bag 11 in the container 10. In particular, the container 10 comprises a venting opening or hole 30 which is opened before or during first use.

The inhaler 4 comprises a delivery mechanism, preferably a pressure generator 12, for conveying and nebulizing the fluid 9, particularly in a preset and optionally in an adjustable dosage amount.

The inhaler 4 or pressure generator 12 comprises preferably a holder 13 for releasably holding the container 10, a drive spring 14 associated to the holder 13, only partly shown, and/or a blocking element 15 preferably in form of or with a button for preferably manual actuation or depressing. The blocking element 15 can catch and block the holder 13 and can be manually operated to release the holder 13 allowing drive spring 14 to expand.

The inhaler 4 or pressure generator 12 comprises preferably a conveying element, such as a conveying tube 16, a non-return valve 17, a pressure chamber 18 and/or a nozzle 19 for nebulizing the fluid 9 into the mouthpiece 3.

The completely inserted container 10 is fixed or held in the inhaler 4 via the holder 13 such that the conveying element fluidically connects the container 10 to the inhaler 4 or pressure generator 12. Preferably, the conveying tube 16 penetrates into the container 10.

The inhaler 4 or holder 13 is preferably constructed so that the container 10 can be exchanged.

When the drive spring 14 is axially tensioned in the tensioning process, the holder 13 with the container 10 and the conveying tube 16 are moved downwards in the drawings and fluid 9 is sucked out of the container 10 into the pressure chamber 18 of the pressure generator 12 through the non-return valve 17. In this state, the holder 13 is caught by the blocking element 15 so that the drive spring 14 is kept compressed. Then, the inhaler 4 is in the tensioned state.

If actuation or pressing of the blocking element 15 was possible (which is not the case when the inhalation training device 1 is attached to the inhaler 4) a relaxation would follow in the nebulization process, during which the fluid 9 in the pressure chamber 18 would be put under pressure as the conveying tube 16 with its then closed non-return valve 17 would be moved back in the pressure chamber 18, here in the drawings upwards, by the relaxation or force of the drive spring 14 and then would act as a pressing ram or piston. This pressure would force the fluid 9 through the nozzle 19, whereupon it would be nebulized into an aerosol and, thus, dispensed.

Generally, the inhaler 4 operates with a spring pressure of 5 to 200 MPa, preferably 10 to 100 MPa on the fluid 2, and/or with a volume of fluid 2 delivered per stroke of 10 to 50 preferably 10 to 20 μl, most preferably about 15 μl. The fluid 9 is converted into or nebulized as aerosol, the droplets of which have an aerodynamic diameter of up to 20 μm, preferably 3 to 10 μm. Preferably, the generated jet spray has an angle of 20° to 160°, preferably 80° to 100°.

The inhaler 4 comprises preferably a housing 31 and/or (upper) housing part 23 and optionally a biasing or inner part 24 preferably which is rotatable relative thereto (FIG. 4) and/or has an upper part 24*a* and a lower part 24*b* (FIG. 3).

The inhaler 4 or housing 31 comprises preferably a (lower) housing part 25. This part 25 is in particular manually operable, and/or releasable fixed, particularly fitted or held onto the inner part 24, preferably by means of a retaining element 26.

Preferably, the housing parts 23 and 25 and/or other parts form the housing 31 of the inhaler 4.

In order to insert and/or replace the container 10, preferably the housing 31 can be opened and/or the housing part 25 can be detached from the inhaler 4, inner part 24 or housing 31.

Generally and preferably, the container 10 can be inserted before the housing 31 is closed and/or before the housing part 25 is connected to the housing 31. Preferably, the container 10 is inserted, opened and/or fluidically connected to the delivery mechanism automatically or simultaneously when (completely) connecting the housing part 25 to the housing 31/inhaler 4 and/or when (completely) closing the housing 31/inhaler 4.

Preferably, the inhaler 4 or drive spring 14 can be manually activated or tensioned, in particular by actuation of an actuation member, here preferably by rotating housing part 25 or any other component.

The actuation member, preferably the housing part 25, can be actuated, here rotated relative to the upper housing part 23, carrying with it or driving the inner part 24. The inner part 24 acts on a gear or transmission to transform the rotation in an axial movement. As a result, the drive spring 14 is tensioned in the axial direction by means of the gear or transmission (not shown) formed between the inner part 24, in particular its upper part 24*a*, and the holder 13 and acting on the holder 13. During tensioning the container 10 is moved axially downwards until the container 10 assumes an end position as shown in FIG. 4. In this activated or tensioned state the drive spring 14 is under tension and can be caught or held by the blocking element 15. During the nebulizing process the container 10 is moved back into its original position (non-tensioned position or state shown in FIG. 3) by (the force of) the drive spring 14. Thus, the container 10 executes a lifting or stroke movement during the tensioning process and during the nebulizing process.

The housing part 25 preferably forms a cap-like lower housing part and/or fits around or over a lower free end portion of the container 10. As the drive spring 14 is tensioned the container 10 moves with its end portion (further) into the housing part 25 or towards the end face thereof, while an aeration means, such as an axially acting spring 27 arranged in the housing part 25, comes in contact with base 28 of the container 10 and pierces the container 3 or a base seal or foil 50 thereon with a piercing element 22 when the container 3 makes contact with it for the first time, to allow air in or aeration, preferably by opening or piercing venting hole 23.

The inhaler 4 comprises preferably an indicator device 25, which counts in particular actuations of the inhaler 4, preferably by detecting tensioning of the drive spring 14 or the rotation of the inner part 24 relative to the upper part 23 or housing 31. Preferably, the counter device 32 or an associated locking device 33 locks the inhaler 4 against (further) actuation or use, e.g., blocks further rotation of the housing part 25/inner part 24 and, thus, tensioning of the inhaler 4 or its drive spring 14 and/or blocks actuation of the blocking element 15, in a locked state when a certain number of actuations or operations or discharged doses has been reached or exceeded.

Unlike freestanding equipment or the like, the inhaler 4 is preferably designed to be portable, and in particular, is a portable hand operated device.

Preferably, the fluid 9 is an aqueous pharmaceutical formulation or an ethanolic pharmaceutical formulation. However, it may also be some other pharmaceutical formulation, a suspension or the like.

Alternatively, the fluid 9 may also comprise particles or powder. In this case, instead of the expulsion nozzle 17, some other kind of supply device may be provided, especially an expulsion opening (not shown) or a supply channel (not shown) for supplying the fluid to or powder or the like into the mouthpiece 3. An optional air supply opening (not shown) then serves to supply ambient air preferably in parallel so as to generate or allow an airflow with a sufficient volume for breathing in or inhaling through the mouthpiece 3.

If necessary, the fluid 9 may also be atomized by means of a propellant gas.

Preferred ingredients and/or formulations of the preferably medicinal fluid 9 are listed in particular in WO 2009/115200 A1, preferably on pages 25 to 40, and in corresponding U.S. Pat. No. 8,650,840, or in EP 2 614 848 A1, paragraphs [0040] to [0087], which are incorporated herein by reference. In particular, these fluids may be aqueous or non-aqueous solutions, mixtures, formulations containing ethanol or free from any solvent, or the like.

FIG. 5 schematically shows a perspective view of a preferred embodiment of an inhalation training system 35 according to the present invention.

The inhalation training system 35 is used or usable or designed for practicing of an inhalation process of a patient.

The inhalation training system 35 comprises the inhalation training device 1 as described above, an inhaler 4 preferably as described above, and a separate and/or mobile electronic device 7, preferably a smartphone.

The smartphone 7 is configured for evaluation of a signal received from the inhalation training device 1 and for visual and/or audio feedback to the patient, in particular via a display 7a, a loud speaker 7b or the like.

The purpose of the inhalation training system 35 is to further educate the patient to inhale correctly with the range of inhalers. Due to the preferred soft mist technology of the inhalers which generate a homogeneous droplet aerosol cloud of 1 to 1.5 seconds duration and where the instructions for correct inhalation is to inhale with relative low flow over an extended period of time, some patients may potentially be confused on correct use as they previously might have been subjected to other inhalers specifically requiring them to inhale forcefully and with only very short duration (e.g., passive dry powder inhalers).

The inhalation training system 35 enables an effective, simple, reliable, comfortable and cost-efficient training of an inhalation process of a patient and a precise measurement of a flow generated by the patient during training and a patient-friendly real-time feedback.

In the preferred embodiment, the inhalation training system 35 is configured to non-invasive detection (i.e., with unchanged flow resistance of the inhaler 4) of correct inhalation flow in the range of at least 20 to 40 l/min with an accuracy of at least +/−50% but preferably better than +/−20%.

The electronic device 7 is configured preferably to detect the presence of the inhalation training device 1 by means of the reference tone generated by the inhalation training device 1 during training as described above. Thus, the electronic device 7 can detect if an inhalation training device 1 has been plugged via connector 8 into the electronic device 7. The electronic device 7 is configured to not provide any feedback related to flow detection if this is not the case.

The electronic device 7 is capable of interfacing to the external microphone 5 of the inhalation training device 1.

In the preferred embodiment, the electronic device 7 is equipped with a dedicated App which in combination is capable of real-time measuring and displaying information (preferably via display 7a) related to patient inhalation flow thereby providing feedback regarding correct and incorrect inhalation techniques.

The App presents flow feedback to the patient in a simple and intuitive manner (non-scientific) and is available for download onto the electronic device 7. For this purpose, the App is developed for all main platforms, especially iOS and Android.

Even if the App has been developed to contain all technical analysis capabilities as presented above, the App is targeted at a very broad audience of patients and hence leverages a very simple and intuitive user interface. Preferably, the App and/or electronic device 7 are adapted to give an audible and/or visible feedback, preferably via the display 7a of the electronic device 7 and/or most preferably by showing one or more respective symbols 7, such as a balloon or the like, which can be easily understood by most people (compare FIG. 5 which shows as an example a balloon as symbol 7d for indicating the inhalation process or the like).

In particular, a balloon concept was finally chosen as the core element to provide feedback regarding patient inhalation flow pattern. According to this concept, the patient's inhalation flow rate determines the balloon flight level. If the patent performs a forceful inhalation (e.g., more than 60 l/min) the balloon will fly high on the screen, whereas a very weak inhalation (e.g., less than 10 l/min) will result in the balloon hovering at the bottom of the screen. In the center range of 20-40 l/min the balloon shifts color from red (amber) to green and two sharp arrows start to close in from the sides. After two seconds of correct flow rate the arrows puncture the balloon thereby indicating a successful inhalation. When the balloon pops the screen turns to a 10 seconds countdown clock allowing training of breath holding following inhalation (similar to the use instructions).

The App is split in two parts, a passive guide part and an active training part, and the patient is carefully introduced to the guide before being subject to real training.

The patient initially accept the terms of use and then enters into the guide part of the App where he is carried through all patient related installation steps of mounting the inhalation training device 1 over the mouthpiece 3 of the inhaler 4 and plugging the connector 8 into the electronic device 7. The patient is introduced to the features of the App using animated screens of both balloon flying and breath holding. At any point in the guide the patient may press a highlighted 'X' to exit the guide and begin training, otherwise he will on the very last guide page be redirected to the training part of the App by simple button confirmation to 'Start training'. When entering the training part the App requires the presence of the inhalation training device 1 to function. If the inhalation training device 1 is not mounted then a warning will be presented to the patient.

Generally, the user or patient could also press a button 7c, the touch screen or the like of the electronic device 7 for input or confirmation purposes.

Then, the flow training takes place by inhaling through the inhalation training device 1 mounted over the inhaler 4 and completing the quest to balance the balloon in the 'green' zone for two seconds and following to hold the breath for 10 seconds. After successfully having completed both steps, the green colored symbol will fly into a history bar showing the last five attempts. Since the App has no means to detect the patient holding his/her breath, the last step in this training sequence will never be able to disqualify an otherwise perfect inhalation sequence only the final result adding to the history awaits the 10 seconds delay.

Since the primary training objective of the inhalation training device 1 is to help patients reduce inhalation flow to a much lower level than, e.g., required with a passive DPI the one element that can cause an unsuccessful inhalation is if the patient inhales too strongly (above 40 l/min) for two seconds (or longer). In this situation the inhalation sequence will be unsuccessful and the negative result will be added directly to the history without going through the sequence of breath holding.

After every test completion, successful or unsuccessful, the patient is presented with the option to 'Try again' to motivate him/her to continue training until he/she safely and reliably can balance the balloon right every time (at least for five consecutive trials).

Instructions are preferably stored on an information storage medium and when executed by a processor cause the execution of the steps described above.

Other steps can be added to the described steps of the App. Individual steps of the App can also be omitted. The sequence of the individual steps can be changed and different steps can be combined with one another. Individual steps of the App can also be implemented independently of other steps.

Flow measurement accuracy also depends on the production tolerances of the microphone 5 which potentially could exhibit +/−3 dB variation in acoustic sensitivity. If no other sources to error did exist such microphone tolerance variation would translate to a measuring uncertainty around +/−35%. This uncertainty does not appear to be critical to perform the inhalation training process where e.g., a measuring uncertainty of +/−50% has been communicated being acceptable.

To mitigate the microphone tolerance variation, the microphone gain and/or the reference tone amplitude can be calibrated. Preferably, each electronics module including the microphone 5 is subjected (prior to mounting in the housing 2 of the inhalation training device 1) to a test using a reference acoustic signal allowing assessment of variation from ideal reference. In case of deviations, e.g., the reference tone amplitude is adjusted to produce the desired relation to the measured microphone signal. Adjustment could be as simple as cutting a wire on the carrying flexible printed circuitry board (cutting, e.g., a parallel resistor controlling reference voltage attenuation).

Alternatively, the final assembled inhalation training device 1 could be tested to create a code based on the individual acoustic deviation. The code can then be imported into the App prior to use. For example, the inhalation training device 1 can have an individual serial number containing a single digit reference to categorize the inhalation training device 1. In order to improve measuring accuracy the patient can manually enter the code upon start of the App. Alternatively, a barcode can be printed on the housing 2 of the inhalation training device 1. The patient can then scan the barcode with a camera of the smartphone 7 during the initialization procedure of the App.

FIG. 5 shows another preferred aspect of the present invention. Preferably, the inhalation training device or its housing 2 comprises the blocking device 2c for blocking any dispensing of fluid 9 by the inhaler 4 when the inhalation training device 1 is mounted to or with the inhaler 4. Preferably, the blocking device 2c covers an actuation element or button, such as blocking element 15 of the inhaler 4 in order to block or prevent any possible actuation and, thus, any possible dispensing of fluid 9. However, other construction solutions are possible as well.

Preferably, the inhalation training device 1 does not (significantly) amend or restrict the flow of air which is drawn through the at least one opening 34 into the mouthpiece 3 during inhalation. However, the microphone 5 might protrude into an associated opening 34 and/or is preferably located adjacent, most preferably as near as possible, to one venting opening 34.

In the embodiment, the inhalation training device 1 or its housing 2 does not cover the other opening 34. For this purpose, the inhalation training device 1 or housing 2 comprises preferably a recess 2d as indicated in FIGS. 1 to 3.

In order to not restrict flow of air that is sucked through opening(s) 34 into the mouthpiece 3 during inhalation, the inhalation training device 1 or its housing 2 comprises preferably at least one supply opening 2e or the like as schematically shown in FIGS. 1 and 3.

Preferably, the cable 6 is guided within the inhalation training device 1 or its housing 2 from the mouthpiece 3 towards the other end of the inhaler 4, preferably through the blocking device 2c and/or preferably thinner like portions or sections 2ac and/or 2bc.

Preferably, the microphone 5 and electronics 5a form a unit or assembly. In particular, the electronics 5a is integrated into the microphone 5 or vice versa.

Preferably, the training inhalation device 1 or its housing 2 holds the unit or assembly of microphone 5 and/or electronics 5a by snap-fit and/or form-fit. A possible realization is indicated in FIG. 3 schematically. For example, the unit or assembly can be inserted into or through a holding recess 2f or the like or mounted, with the microphone 5 preferably pointing towards the mouthpiece 3, adjacent to air vent opening 34 and/or adjacent to the nozzle 19 of the inhaler 4 and/or pointing radially inwards.

Preferably, the blocking device 2c is supported or abuts against the inhaler housing 31, preferably an upper housing part 23 of the inhaler 4. For this purpose, the blocking device 2c or section 2ac may comprise a respective protrusion or contact portion 2ca as indicated in FIGS. 4 and 5.

Preferably, the blocking device 2c covers the blocking element 15 or any other actuation element, necessary for triggering or initiating dispensing of fluid 9 from the nebulizer 4, preferably completely, such that any dispensing of fluid 9 from the inhaler 4 is securely prevented when the inhalation training device 1 is mounted to the inhaler 4 or vice versa.

What is claimed is:

1. An inhalation training system for practicing of an inhalation process of a patient, the inhalation training system comprising:
   an inhalation training device;
   an inhaler constructed to provide a drug to the patient and having a mouthpiece at an outlet end thereof; and
   an electronic portable communications device configured for evaluation of an electronic signal received from the inhalation training device and for visual and audio feedback to the patient;
   wherein the inhalation training device comprises:
   a housing attachable to and detachable from the mouthpiece of the inhaler;
   a microphone adapted to directly measure sound produced by the airflow occurring in the mouthpiece of the inhaler during an inhalation process of the patient and from which said electronic signal is produced; and
   interface means for communicating the electronic signal to the electronic portable communications device,
   wherein the housing is constructed to prevent drug release during training by a finger-shaped blocking device covering an actuation element of the inhaler.

2. An inhalation training device for practicing of an inhalation process of a patient, the inhalation training device comprising a housing attachable to and detachable from a mouthpiece of an inhaler constructed to provide a drug to the patient,
   wherein the housing has a finger-shaped blocking device covering an actuation element of the inhaler in a manner acting to prevent drug release during an inhalation process of the patient, and
   wherein the inhalation training device comprises a microphone adapted to directly measure sound produced by the airflow occurring in the mouthpiece of the inhaler during an inhalation process of the patient, and
   wherein the microphone is positioned at a location in the inhalation training device that will be adjacent to an air-vent or nozzle of the mouthpiece of the inhaler, when the housing of the inhalation training device is attached to the mouthpiece of the inhaler, and removed from the inhaler, when the housing of the inhalation training device is detached from the mouthpiece of the inhaler.

3. The inhalation training device according to claim 2, wherein the housing comprises at least one of a pad and a sleeve around the microphone that is made of foam plastic or soft silicone.

4. The inhalation training device according to claim 2, wherein the microphone is adapted to measure the noise of the airflow through the air-vent or nozzle of the mouthpiece of the inhaler.

5. The inhalation training device according to claim 2, wherein the microphone is a directional or bi-directional microphone.

6. The inhalation training device according to claim 2, wherein the microphone is adapted to produce an electronic signal and the inhalation training device has an interface for communicating the electronic signal to an electronic portable communications device.

7. The inhalation training device according to claim 6, wherein the interface comprises a TRRS headset connector and wherein the inhalation training device comprises electronics configured to swap the electric connection to the microphone and to ground in dependence of a connection scheme of the TRRS headset connector.

8. The inhalation training device according to claim 6, wherein the inhalation training device comprises electronics configured to adjust a frequency range in which the microphone operates as a function of an analog front-end sensitivity of the electronic portable communications device.

* * * * *